US00PP10493P

United States Patent [19]

Holtkamp, Sr.

[11] Patent Number: Plant 10,493

[45] Date of Patent: Jul. 14, 1998

[54] AFRICAN VIOLET PLANT NAMED PICASSO

[75] Inventor: Reinhold Holtkamp, Sr., Rees-Haffen, Germany

[73] Assignee: International Plant Breeding A.G., Bern, Switzerland

[21] Appl. No.: 798,299

[22] Filed: Feb. 7, 1997

[51] Int. Cl.[6] ..... A01H 5/00

[52] U.S. Cl. ..... Plt./69.1

[58] Field of Search ..... Plt./69.1

*Primary Examiner*—James R. Feyrer
*Assistant Examiner*—Melissa L. Kimball
*Attorney, Agent, or Firm*—Foley & Lardner

[57] ABSTRACT

A new and distinct cultivar of African violet named Picasso, as described and illustrated, and particularly characterized by its single violet-shaped, multi-colored pink flowers with brighter pink center and purplish blue speckles on the petals; strong, upright flower stems that curve slightly toward the center to form a compact bouquet above the leaves; medium green, heart-shaped leaves; profuse flowering; vigorous and compact growth habit; flowering 9–10 weeks after potting, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Picasso.

The new cultivar was referred to during the breeding and selection process by the designation O 4-9/51 and is a product of a planned breeding program. The new cultivar was originated from a cross made by me in the controlled breeding program in Haffen, Federal Republic of Germany. The female, or seed parent was a cultivar designated AS 24 pink *. The male, or pollen parent was a cultivar designated 88 M.

Picasso was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Picasso has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Picasso, which in combination distinguish this African violet as a new and distinct cultivar:

(1) Strong, upright flower stems curving slightly toward the center.

(2) Single violet-shaped, multi-colored flowers which are pink with a brighter pink center and purplish blue speckles.

(3) Profuse flowering.

(4) Each plant carries 10–12 and more upright flower stems each of which carries 10–12 and more flowers.

(5) Long lasting, non-dropping flowers.

(6) Vigorous and compact grower.

(7) Plant saleable 9 to 10 weeks after potting.

(8) Seed capsules push slightly through.

(9) Medium green, heart-shaped, slightly serrated leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (RHS), except where general colors of ordinary significance are referred to. Color values were taken under natural sunlight conditions at approximately 12 p.m. in Nashville, Tenn.

Botanical Classification: *Saintpaulia ionantha*, Ramat., c.v. Picasso.

Parentage:

*Male parent.*—88 M.

*Female parent.*—AS 24 pink *.

Propagation: The new cultivar holds its distinguishing characteristics through successive propagations by leaf cuttings.

Plant: From 9 cm to 11 cm tall when grown in pots, and 24–28 cm in diameter when fully grown.

*Leaves.*—General form: Heart-shaped. Diameter: 55–65 mm wide and 60–70 mm long. Texture: Velvety. Aspect: Hairy, slightly serrated, slightly shiny. Veins: Upperside: visible; underside: well pronounced, light green (on young leaves purplish red), shiny. Color (upperside): Yellow-Green Group 147 A. Color (underside): Greyed-Green Group 194 D. Petiole: Strong, green to purplish brown, hairy.

*Flowers.*—Buds: Bell-shaped, light green with pinkish touch and purplish blue speckles, 5–7 mm just before opening. Sepals: Five (5). Color: Green with purplish brown touch. Calyx: Shape: Funnel-shaped. Aspect: Spear-shaped, hairy. Peduncle: Character: Strong upright, hairy. Color: Purplish brown.

*Individual flowers.*—Size: 35–40 mm. Shape: Single violet-shaped. Color (upperside): Purple Group 78 B to C with center being Red-Purple 74 B to C. Speckles are Violet Group 88 A to B. Under cooler temperatures and more intensive lighting, the pink tends to intensify. Color (underside): Purple Group 78 C to D with speckles being Violet Group 88 B to C. Borne: Each flower stem carries 10–12 and more flowers on strong, upright peduncles that are free standing above the leaves, thereby forming a compact bouquet. Flowering habit: Flowers 9–10 weeks after potting.

*Reproductive Organs.*—Stamens: Two (2). Anthers: 2 composed of 4 anther cells, seed capsules push slightly through. Filaments: Yellowish white, 3–4 mm long. Pollen Color: Yellow Group 7 A. Styles: 6–7 mm long, purplish pink, base of ovary light green and hairy.

*Roots.*—Normally developed, white when young, turning slightly brownish when older.

Disease resistance: Up to date, Picasso has shown very good resistance to all major violet diseases.

General observations

Picasso is an attractive cultivar due to its interesting multi-colored flowers which are pink with a brighter pink center and purplish blue speckles on the petals. A tight bouquet of flowers free standing above the leaves develops 9–10 weeks after potting. Each of the 10–12 and more strong flower stems carries 10–12 and more single violet-shaped flowers, occasionally having an additional very small petal in the center. Medium green, heart-shaped, slightly serrated leaves surround the flower bouquet. The flowers are long-lasting and non-dropping and the seed capsules push slightly through.

I claim:

1. A new and distinct cultivar of African violet plant named Picasso, as described and illustrated, and particularly characterized by its single violet-shaped, multi-colored pink flowers with brighter pink center and purplish blue speckles on the petals; strong, upright flower stems that curve slightly toward the center to form a compact bouquet above the leaves; medium green, heart-shaped leaves; profuse flowering; vigorous and compact growth habit; flowering 9–10 weeks after potting, and by its long lasting and non-dropping flowers.

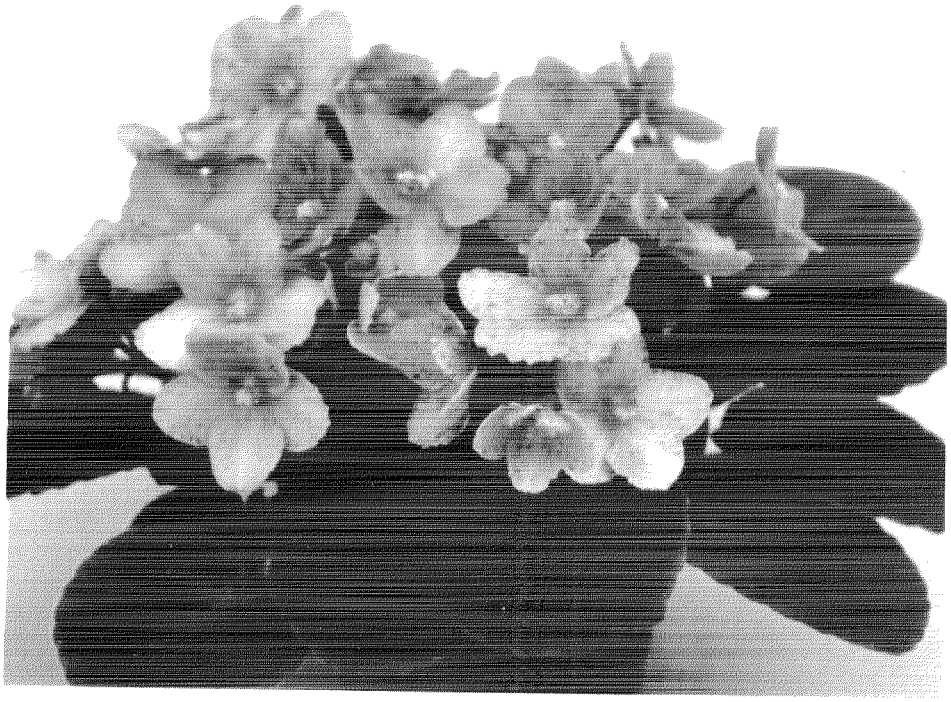

* * * * *